(12) United States Patent
Kuhn et al.

(10) Patent No.: US 8,834,787 B2
(45) Date of Patent: Sep. 16, 2014

(54) SURFACE-ACTIVE METAL COMPLEXES ON CARRIER MATERIAL FOR ADSORBING NOXIOUS SUBSTANCES AND METHOD FOR PRODUCTION THEREOF

(75) Inventors: Hubert Kuhn, Solingen (DE); Gordon Thie, Hattingen (DE)

(73) Assignee: CAM-D Technologies GmbH (DE)

( * ) Notice: Subject to any disclaimer, the term of this patent is extended or adjusted under 35 U.S.C. 154(b) by 1011 days.

(21) Appl. No.: 12/809,778

(22) PCT Filed: Nov. 14, 2008

(86) PCT No.: PCT/EP2008/009632
§ 371 (c)(1),
(2), (4) Date: Oct. 29, 2010

(87) PCT Pub. No.: WO2009/083070
PCT Pub. Date: Jul. 9, 2009

(65) Prior Publication Data
US 2011/0123393 A1    May 26, 2011

(30) Foreign Application Priority Data
Dec. 21, 2007  (DE) .................. 10 2007 062 816
Feb. 25, 2008  (DE) .................. 10 2008 010 774

(51) Int. Cl.
*A61L 9/00*     (2006.01)
*C07F 3/00*     (2006.01)

(52) U.S. Cl.
USPC ............................. 422/5; 556/118

(58) Field of Classification Search
USPC ............................. 422/5; 556/118
See application file for complete search history.

(56) References Cited

U.S. PATENT DOCUMENTS

2003/0004364 A1 * 1/2003 Yaghi et al. ............... 556/46

FOREIGN PATENT DOCUMENTS

DE    3808114 A1 *  9/1989

OTHER PUBLICATIONS

English Translation of Document No. DE 3808114 A1 provided by Espacenet: Desai et al.; Compositions with a Deodorant Action; Sep. 21, 1989.*

* cited by examiner

*Primary Examiner* — Kevin Joyner
(74) *Attorney, Agent, or Firm* — Brannon Sowers & Cracraft PC

(57) ABSTRACT

The present invention relates to complexed metal salts which comprise ligands and at least one complexing agent for chemically binding noxious substances and/or odor-forming substances, the ligands comprising a hydrophobic carbon skeleton with hydrophilic groups. The complexed metal salt formed with the complexing agent is water-soluble and surface-active. Preferred complexing agents are water-soluble acids or salts of at least bifunctional acids, or also ether carboxylic acids.

6 Claims, 6 Drawing Sheets

SURFACE-ACTIVE METAL COMPLEXES ON CARRIER MATERIAL FOR ADSORBING NOXIOUS SUBSTANCES AND METHOD FOR PRODUCTION THEREOF

CROSS-REFERENCES TO RELATED APPLICATIONS

This application is a National Stage filing of International Application PCT/EP 2008/009632, filed Nov. 14, 2008, claiming priority to German Applications No. DE 10 2007 062 816.3 filed Dec. 21, 2007, and DE 10 2008 010 774.3 filed Feb. 25, 2008, entitled "SURFACE-ACTIVE METAL COMPLEXES ON CARRIER MATERIAL FOR ADSORBING NOXIOUS SUBSTANCES AND METHOD FOR PRODUCTION THEREOF." The subject application claims priority to PCT/EP 2008/009632, and to German Applications No. DE 10 2007 062 816.3 and DE 10 2008 010 714.3, and incorporates all by reference herein, in their entirety.

BACKGROUND OF THE INVENTION

The present invention relates to complexed metal salts, which will also be referred to as metal complexes in the following, which have at least one ligand and at least one complexing agent, wherein these complexed metal salts are particularly useful for chemically binding and adsorbing noxious and/or odour-producing substances, wherein particularly the ligands have a hydrophobic carbon skeleton with hydrophilic groups. The complexed metal salt formed with the complexing agent is advantageously soluble in water and surface-active. Preferred complexing agents are particularly water-soluble acids or salts of at least bifunctional acids, or also ether carboxylic acids.

The present invention also relates to the production of these complexed metal salts and their use as well as compounds that contain them.

It has long been known that zinc salts of fatty acids, which are also known as zinc soaps, have a de-odourising effect. A known example is the zinc salt of ricinoleic acid, zinc ricinoleate. These zinc salts are capable of chemically binding and thus neutralising the odour of substances such as nitrogen containing substances, which include the amines, or sulphur containing substances, such as thiols or mercaptans, as well as carboxylic acids, such as the strongly odorous compounds isovaleric acid and butyric acid. They are therefore particularly used in cosmetic and home care products.

However, the zinc salts of fatty acids, such as zinc ricinoleate, are insoluble in water, which is why until now it is has been necessary to create complicated formulations that enable the zinc salts to be converted to an aqueous solution or flowable concentrate. Examples of such are deodorants. These formulations are typically based on a large number of auxiliary materials, additives and/or solubilisers that together function as solubilising agents.

GB-PS 1 282 889 describes the use of zinc salts of unsaturated aliphatic hydroxycarboxylic acids having at least 17 C atoms, such as ricinoleic acid, for use as a deodorising medium.

A preparation with deodorising effect that contains the zinc salt of ricinoleic acid, amino-functional acids such as amino acids, solubilisers, organic and/or inorganic acids, and possibly water, is also known from the related art, for example from EP 1 319 394 A1. Tensides or glycols are used as solubilisers.

EP 1 250 938 A2 discloses a water-soluble homecare concentrate with zinc ricinoleate and an alkoxyamine derivative.

A deodorant described in EP 0 303 212 A2 is based on hydrolysed ene adducts and Diels-Alder adducts of ricin fatty acids and maleic anhydride, to which triethanol amine and an organic acid are added, and on a solvent from the alcohol group.

In DE 40 14 055 A1, a substance having deodorising effect is described that is based on the zinc salt of ricinoleic acid and/or the zinc salt of abietic acid and/or additional zinc salts of other saturated or unsaturated hydroxylated fatty acids having 16 and more C atoms, in which an ethoxylated fatty alcohol and a tertiary amine are also contained.

A large number of auxiliary materials and/or additives are needed, depending on the liquid or paste-like odour-adsorbing formulations of the related art, in order to transfer the water-insoluble zinc salts to these formulations.

BRIEF SUMMARY OF THE INVENTION

Accordingly, the object of the present invention is to provide metal soaps, or derivatives of metal soaps, which will be referred to in the following as metal salts, that are capable of binding noxious substances and/or odoriferous substances, wherein these compounds should also be designed to be water-soluble and/or surface-active.

It is further intended to provide a method for producing such metal soaps or metal soap derivatives and the compounds containing them, particularly aqueous compounds.

In order to solve the problem described in the aforegoing, the present invention suggests complexed metal salts, and production methods therefor as described herein. Further objects of the present invention are also compounds described, and the use of the complexed metal salts described below. Further advantageous variations are similarly disclosed.

The object of the present invention according to a first aspect of the invention are thus complexed metal salts, which will also be referred to as metal complexes in the following, wherein the complexed metal salts include at least one ligand and at least one complexing agent, wherein these complexed metal salts are designed to be water-soluble and/or surface-active, and these complexed metal salts are particularly suitable for chemically binding or adsorbing noxious and/or odorous substances. The ligands may include a hydrophobic carbon skeleton having hydrophilic groups. The complexed metal salts that are formed with the complexing agent are soluble in water (unlike the non-complexed, pure metal salts, which are water-insoluble). Water-soluble acids or salts of at least bifunctional acids, or also ether carboxylic acids are used as complexing agents.

DETAILED DESCRIPTION OF THE INVENTION

Figure 1:
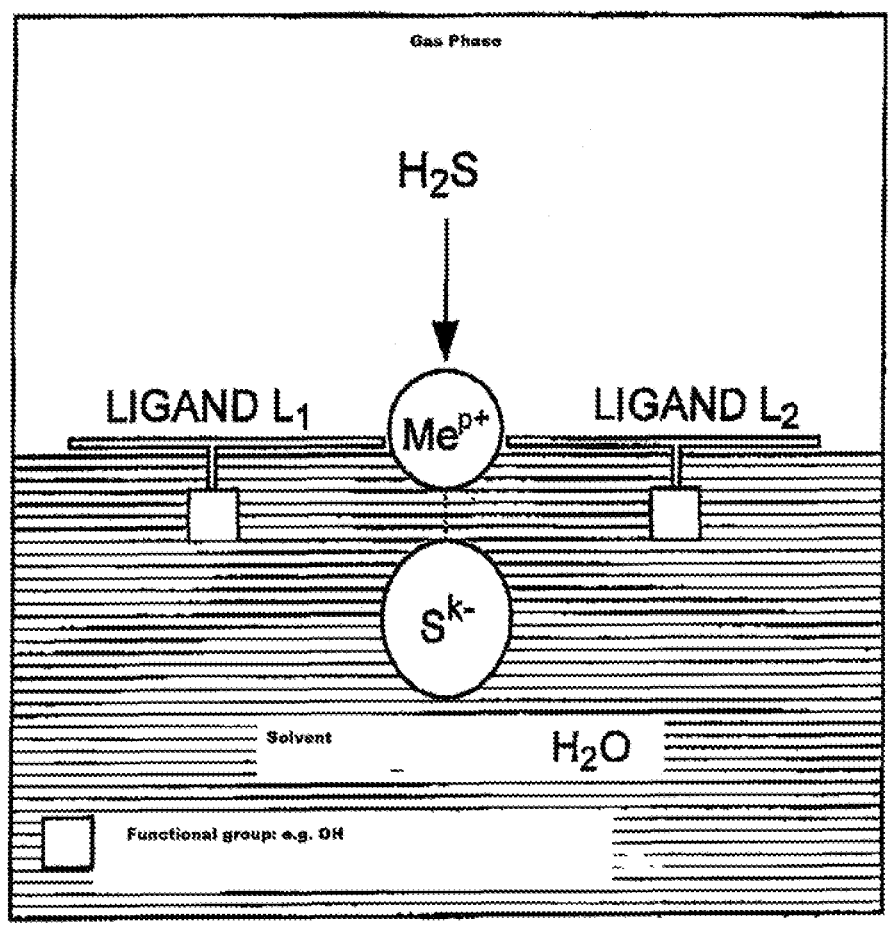
FIG. 1 provides a possible idealised structure of the surface-acting complexes described herein.

The present invention relates particularly to complexed metal salts having ligands and at least one complexing agent for chemically binding noxious and/or odoriferous substances, wherein the ligands generally have a hydrophobic carbon skeleton with hydrophilic groups, particularly at least one hydrophobic alkyl chain with hydrophilic groups. The complexed metal salt formed with the complexing agent is water-soluble and surface-active. Water-soluble acids or salts of at least bifunctional acids, or also ether carboxylic acids are used as complexing agents.

A preferred object of the invention is a complexed metal salt having ligands, particularly for chemically binding noxious and/or odoriferous substances having electron donor properties, wherein noxious substances are understood particularly to include aliphatic and aromatic nitrogen compounds such as amines, ammonia, nitrogen oxides, nitrates and nitrites; these are for example compounds having the following general formulas, wherein the aliphatic and aromatic radicals are indicated by R: $NH_3$, $RNH$, $R_2NH$, $R_3N$, $N_xO_y$, $RNO_2$, $RNO_3"$, $NO_2"$, $NO_3"$. Other noxious substances may be aliphatic and aromatic sulphur compounds such as hydrogen sulphide, thiols, thioethers, sulphonates, sulphites and sulphates, which are represented in idealised form by the following formulas, wherein the aliphatic and aromatic radicals are indicated by R: $H_2S$, $RSH$, $R_2S$, $RSO_3H$, $RSO_4H$, $SO_3^{2-}$, $SO_4^{2-}$. Yet more noxious substances may also be aliphatic and/or aromatic carboxylic acids having formula R—COOH, where R has the meaning indicated above, and/or aliphatic and aromatic phosphorus compounds and inorganic phosphorus compounds.

According to the first aspect, the object of the invention is particularly a complexed metal salt having ligands, particularly for chemically binding noxious and/or odoriferous substances having electron donor properties, wherein the metal is present as a cation and is selected from the group of zinc, copper, iron, cadmium, mercury, molybdenum, lead, cobalt, nickel, chromium, vanadium, manganese, or tungsten, wherein the ligands are derived from compounds having a hydrophobic carbon skeleton with hydrophilic groups, wherein they are typically present in the metal salt as an anion, particularly wherein the ligands are derived from at least one functionalised fatty acid, alkenyl carboxylic acid or aryl carboxylic acid, alkyl sulphonate, aryl sulphonate, alkyl sulphate, aryl sulphate, alkyl phosphate, aryl phosphate, alkyl phosphonate or aryl phosphonate, or from correspondingly alkenyl-, arylalkenyl-, and/or arylalkyl functionalised acids, wherein the alkyl or alkenyl groups are linear, branched, and/or cyclic and have 1 to 40 C atoms, preferably 8 to 35 C atoms, particularly 12 to 25 C atoms, and the aryl group has 6 or 12 C atoms, wherein the alkyl, alkenyl and/or aryl groups are functionalised with at least one of the hydrophilic groups, particularly wherein the alkyl, alkenyl and/or aryl groups may be multiply functionalised, they particularly preferably have from 1 to 20, preferably from 1 to 10 functional groups, particularly at least one of the following groups, such as —OH, $SO_3^-$, $SO_3H$, $SO_4^-$, $SO_4H$, $COO^-$, $COOH$, $PO_3^-$, $PO_3H$, $PO_4^-$, $PO_4H$; O-(alkyl-O-)$_a$-alkyl-OH where a=1 to 200, preferably 1 to 100, and having alkyl=methyl-, ethyl- or propyl group, SH, S", SR, $NO_2$, $NO_3^-$, $NH_2$, NHR, $NR_2$, $NH_3^+$, $NH_2R^+$, $NHR_2^+$, where R=hydrocarbon radical, glycol, glycerol, polyglycol, polyglycerol; F, Cl, I and/or Br;

and with at least one complexing agent that corresponds to a water-soluble acid, anion, and/or salt of at least one bifunctional to polyfunctional acid or ether carboxylic acid.

In this way, the complexed metal salt may be present as a double salt in the solid.

According to the invention, the uncomplexed metal salt consisting of metal and ligand is water-insoluble.

For the purposes of the present invention, ligands may be compounds having a hydrophobic carbon skeleton with hydrophilic groups, which particularly monofunctionally as a ligand form a metal salt with the metal cation. Preferred ligands have at least one hydrophobic alkyl chain with hydrophilic groups. As are rule, these ligands are water-insoluble, at least the metal salts according to the invention that are formed therewith are water-insoluble without a solubiliser.

For the purposes of the invention complexing agents are understood to be compounds that form a coordinate and/or ionic bond between an acceptor (Lewis acid) and a donor (Lewis base), wherein particularly in the case of the coordinate bond the bonding electrons originate from only one of the two bonding partners, and wherein the complexing agents according to the invention correspond to a water-soluble acid, an anion or salt of an at least bifunctional to polyfunctional acid or ether carboxylic acid. Unlike the ligands, the complexing agents only have a relatively small carbon skeleton, that is to say they typically do not have a hydrophobic alkyl chain. According to the invention, the complexing agents identified form a coordinate and/or ionic bond with the metal through one of their acid functions.

In particular, the complexing agent is selected from the group of water-soluble acids, anions or salts of bi-, tri-, poly-carboxylic acids, bi-, tri-, polyphosphonic acids, bi-, tri-, poly-sulphonic acids, bi-, tri-, polysulphates, di-, tri-, poly-phosphates, polyether carboxylic acids and/or mixed functional compounds of the acids, anions and/or salts. The term ether carboxylic acid, particularly polyether carboxylic acids is understood to include carboxylic acids having the composition alkyl-(O-alkyl)$_c$-COOH or alkyl-(O-alkyl)$_c$-alkyl-COOH where c is equal to 1 to 200, particularly between 1 to 100, preferably having 1 to 15 C atoms.

Particularly suitable complexing agents are the following acids or salts thereof such as oxalic acid, oxalates such as disodium oxalate, tartaric acid (meso, D and/or L) and their salts, aspartic acid, ether carboxylic acids such as for example $CH_3$—$(CH_2)_7$—$(O$—$CH_2$—$CH_2)_8$—COOH or $CH_3$—$(CH_2)_7$—$(O$—$CH_2$—$CH_2)_5$—COOH, ethylene dinitrilotetraacetic acid salt, such as ethylene dinitrilotetraacetic tetrasodium salt, or 1-hydroxyethylidene-(1,1-diphosphonic acid)-disodium salt.

The complexed metal salt lends itself extremely well to chemically bonding noxious and/or odoriferous substances, particularly noxious and/or odoriferous substances with electron donor properties. It is particularly preferred if the complexed metal salt is water-soluble, particularly due to the complexing agents, preferably due to the deprotonised complexing agents, which may be present in solution as an anion or salt and retain their deodorising properties. The complexed metal salt also becomes surface-active due to the substitution pattern of the ligands, which have both hydrophobic and hydrophilic moieties.

FIG. 1 is an idealised, formalised representation of a possible structure of the surface-active complexes, and its mode of action is explained based on the example of a generic metal salt $L_1$-Me-$L_2$ that has been reacted with a complexing agent S to yield a complexed metal salt anion $[[L_1\text{-Me-}L_2]\text{-}S^k]$.

According to a further object of the invention, a complexed metal salt having general formula I

(I)

is provided,
- wherein Me=zinc, copper, iron, cadmium, mercury, molybdenum, lead, cobalt, nickel, chromium, vanadium, manganese or tungsten;
- wherein p=1, 2, 3, 4, 5 or 6, and p corresponds to the oxidation number of Me;
- wherein L is a ligand, and the ligands are derived from compounds having a hydrophobic carbon skeleton and hydrophilic groups, wherein they are normally present as an anion in the metal salt, particularly wherein the ligands are derived from at least one functionalised fatty acid, alkenyl carboxylic acid, alkyl sulphonate, aryl sulphonate, alkyl sulphate, aryl sulphate, alkyl phosphate, aryl phosphate, alkyl phosphonate or aryl phosphonate or from correspondingly functionalised alkenyl-, arylalkenyl and/or arylalkyl acids, wherein L may be identical or different, and wherein 1≤n≤20, particularly wherein 1≤n≤10, and the ligand L is derived from a molecule having general formula II

(II)

having a functional group D, through which according to the invention the metal salt is formed with Me, wherein D=-COOH, —O—SO$_3$H, —SO$_3$H, —O—PO(OH)$_2$, (—O—)$_2$—PO(OH) or —PO(OH)$_2$ and/or an anion or salt derived therefrom, wherein m in formula I corresponds to the charge number of functional group D as an anion or in the salt with m=1, 2, 3 or 4, particularly m=1 and l=1 or 2, wherein $R^1$ corresponds to an organic radical functionalised with B and $R^1$=substituted linear, branched and/or cyclic alkyl, alkenyl, alkylaryl, arylalkyl, alkenylaryl group having 1 to 40 C atoms, preferably 8 to 35 C atoms, particularly 12 to 25 C atoms, and the aryl group has 6 or 12 C atoms, wherein $R^1$ has at least one group B, particularly on a primary, secondary and/or tertiary C atom, particularly preferably on a secondary C atom of an alkyl group, wherein $R^1$ particularly preferably has a plurality of groups B, particularly 1 to 20, preferably 1 to 10, wherein B=OH, SO$_3^-$; SO$_3$H, SO$_4^-$, —O—SO$_3$H, —COOH, PO$_3^-$, PO$_3$H$_4$, PO$_4^-$, PO$_4$H, such as for example —O—PO(OH)$_2$, (—O—)$_2$—PO(OH) or —PO(OH)$_2$ and/or corresponding anions; —O-(alkyl-O-)$_a$-alkyl-OH where 1≤a≤200, preferably 1≤a≤100, and where alkyl=methyl, ethyl, or propyl group, such as —O—(CH$_2$CH$_2$—O—)$_a$—CH$_2$—CH$_2$—OH or —O—(CH$_2$—O—)$_a$—CH$_2$—OH; —SH, —SR, NO$_2$, NO$_3$, —NH$_2$, —NHR$^2$, —NR$^2_2$, —NH$_3^+$, —NH$_2$R$^{2(+)}$, —NHR$^2_2{}^{(+)}$, —F, —Cl, —I, —Br, glycol, glycerol, polyglycol and/or polyglycerol and/or anions or salts derived therefrom, wherein $R^2$ is the same or different and corresponds to a linear, branched and/or cyclic alkyl, alkenyl, alkylaryl group having 1 to 40 C atoms, preferably 1 to 30 C atoms, particularly 1 to 24 C atoms, and the aryl group has 6 or 12 C atoms;

with at least one complexing agent S of a water-soluble acid, for example H$_k$S where H=A, or of a water-soluble anion and/or of a water-soluble salt such as A$_k$S, of an at least bifunctional acid or ether carboxylic acid, wherein S is selected from the group of water-soluble acids, anions and/or salts of the bi-, tri-, polycarboxylic acids, bi-, tri-, polyphosphonic acids, bi-, tri-, polysulphonic acids, bi-, tri-, polysulphates, di-, tri-, polyphosphates and/or polyether carboxylic acids and/or mixed functional compounds of the acids, anions and/or salts, where x=1, 2, 3 or 4 and wherein k corresponds to the charge number of the anion of S, where 1≤k≤20, particularly wherein the charge number of the anion is between 2 and 15, preferably between 2 and 10, wherein ether carboxylic acids are particularly understood to include carboxylic acids having the composition alkyl-(O-alkyl)$_c$-COOH or alkyl-(O-alkyl)$_c$-alkyl-COOH where c is equal to 1 to 200 C atoms, particularly between 10 to 100 C atoms, preferably having 1 to 15 C atoms; and wherein A is the same or different and corresponds to a hydrogen proton, an organic cation and/or a metal cation, particularly an alkaline earth or alkaline metal cation, and where z is equivalent to a whole number between 0≤z≤20, particularly z=1, 2, 3 or 4, and wherein y corresponds to the charge number of A, particularly of the hydrogen or the cation, with y=1, 2 or 3, preferably y=1 or 2, particularly y=1 for the hydrogen proton or an alkali cation, such as Li$^+$, K$^+$, Na$^+$, or y=2 for an alkaline earth cation, such as Ca$^{2+}$ and Mg$^{2+}$, or also a number between 1 and 6, wherein particularly the amount may be from x·k=z·y and/or n·m=p.

In this context, it is preferable if only one acid function of the complexing agent, particularly the deprotonised acid function forms a coordinate and/or ionic bond directly with the metal atom, particularly with Me, as the anion, particularly of the complexing agent S.

As was described earlier, according to the invention the uncomplexed metal salt consisting of metal and ligand is water-insoluble.

On the other hand, the complexed metal salt is water-soluble according to the invention when an ether carboxylic acid, the anion thereof and/or a salt with an acid function forms a coordinate and/or ionic bond with the metal, wherein the metal salt is water-insoluble particularly before complexing.

According to the invention, the complexed metal salt is water-soluble when the complexing agent with an acid function, particularly the complexing agent S, forms a coordinate and/or ionic bond with the metal, and at least one, particularly a second, preferably several, particularly preferably all remaining acid functions of the complexing agent are deprotonised or present as an anion in a salt, particularly wherein A=organic cation or metal cation, wherein the cation is particularly preferably an alkaline or alkali earth cation such as Li$^+$, K$^+$, Na$^+$, Mg$^{2+}$ or Ca$^{2+}$, or alternatively the complexed metal salt is present and solvated in an aqueous solution, particularly as an anion. The aqueous solution, which contains the complexed metal salt, particularly as an anion, has preferably been alkalised with a base such as NaOH, NH$_4$OH, Mg(OH)$_2$ or another common base. The pH value is preferably in the range from greater than 7 up to 12, especially between 7.5 and 11, particularly preferably between 7.1 and 8. Alternatively, the complexing agent as a salt, particularly an alkaline or alkali earth salt, may be reacted directly with the metal salt with ligands in the presence of water.

The complexed metal salt is surface-active both as a solid, particularly as $[[L_n{}^{m-}(Me^{p+})]\text{-}S_x{}^{k-}]\cdot zA^{y+}$ or $[[L_n{}^{m-}(Me^{p+})]\text{-}S_x]$ as defined previously, or also as an anion in aqueous solution, such as for example $[[L_n{}^{m-}XMe^{p+})]\text{-}S_x{}^k]$ in particular its is preferably at the solid/liquid, liquid/liquid, liquid/gas interface, and is able to adsorb noxious materials or substances. In this way, the complexes lower the surface tension, and vigorous foaming may occur.

Because of their activity at the interface, the complexed metal salts are able to adsorb pollutants and/or highly odorous substances at the water/gas or water/air, and/or water/oil or water/solvent interface. Surprisingly, this is the only way that the complexed metal salts are able to chemically bind gas-phase compounds containing sulphur and nitrogen and carboxylic acids from the gas phase or atmosphere in an effective manner. The composition of the substituent and/or the conformation of the substituents are necessary in order to render the complexes metal salts surface-active and water-soluble. At the air/water or water/oil or water/solvent interface, the ligands are aligned parallel to the interface, so that the metal becomes sterically accessible for coordinate and/or ionic binding with the pollutant molecules.

However, even in the solid phase the complexed metal salt is able to chemically bind pollutants from organic solvents or the gas phase and/or odoriferous substances, particularly those with electron donor properties.

A further object of the invention is a preferably aqueous solution or compound containing the complexed metal salt, particularly essentially in solution, preferably completely dissolved, especially as the $[[L_n{}^{m-}(Me^{p+})]\cdot S_x{}^{k-}]\cdot zA^{y+}$ or $[[L_n{}^{m-}(Me^{p+})]\text{-}S_x]$ defined previously, or also as an anion in aqueous solution, such as for example $[[L_n{}^{m-}(Me^{p+})]\text{-}S_x{}^{k-}]$, and/or containing the complexed metal salt as a solid, particularly as an alkaline salt (for example as a sodium or potassium salt) or as an alkaline earth salt, for example with calcium or magnesium, or also with other standard gegenions.

It is assumed that the complexed metal salts are formed when a complexing agent is added to a metal salt in the following reactions, represented ideally:

$L_n\text{Me} + q\text{H}_2\text{O} + M_k\text{S} \rightarrow \{[L_n\text{Me}]\text{-SH}_q\}^{(k-q)-} + kM^+ + q\text{OH}^-$     1.

$\{[L_n\text{Me}]\text{-SH}_q\}^{(k-q)-} + q\text{OH}^- \rightarrow \{[L_n\text{Me}]\text{-S}\}^{k-} + q\text{H}_2\text{O}$     2.

When an ether carboxylic acid is used, the following reaction, represented ideally, may take place:

$L_n\text{Me} + \text{R—O(CH}_2\text{CH}_2\text{O)}_n\text{—CH}_2\text{—COOH} + \text{H}_2\text{O} \rightarrow$ $\text{R—O—(CH}_2\text{CH}_2\text{O)}_n\text{—CH}_2\text{—COO-[L}_n\text{Me]}^- + \text{H}_3\text{O}^+$ According to a further aspect of the invention, a method for producing the complexed metal salt is claimed as well as a complexed metal salt such as is obtainable by this method, and also a preferably aqueous compound containing a complexed metal salt that is obtainable by this method, and as described in the aforegoing, wherein a metal salt with ligands is reacted with at least one complexing agent in the presence of water and optionally in the presence of a base, wherein the metal is present in the metal salt as a cation and is selected from the group of zinc, copper, iron, cadmium, mercury, molybdenum, lead, cobalt, nickel, chromium, vanadium; manganese, or tungsten, wherein the ligands are derived from compounds having a hydrophobic carbon skeleton with hydrophilic groups, wherein they are typically present in the metal salt as an anion, particularly wherein the ligands are derived from at least one functionalised fatty acid, alkenyl carboxylic acid or aryl carboxylic acid, alkyl sulphonate, aryl sulphonate, alkyl sulphate, aryl sulphate, alkyl phosphate, aryl phosphate, alkyl phosphonate or aryl phosphonate, or from correspondingly functionalised alkenyl-, arylalkenyl-, and/or arylalkyl acids, particularly wherein the alkyl and/or aryl groups are multiply functionalised, wherein the alkyl groups are linear, branched, and/or cyclic and have 1 to 40 C atoms, preferably 8 to 35 C atoms, particularly 12 to 25 C atoms, and the aryl group has 6 or 12 C atoms, wherein the alkyl, alkenyl and/or aryl groups are functionalised with at least one of following groups: OH, SO$_3^-$, SO$_3$H, SO$_4^-$, SO$_4$H, COO$^-$, COOH, PO$_3^-$, PO$_3$H, PO$_4^-$, PO$_4$H, —O-(alkyl-O-)$_a$-alkyl-OH where 1≤a≤200, preferably 1≤a≤100, and with alkyl, methyl-, ethyl- or propyl group, such as —O—(CH$_2$CH$_2$—O—)$_a$—CH$_2$—CH$_2$—OH or —O—(CH$_2$—O—)$_a$—CH$_2$—OH; SH, S$^-$, SR, NO$_2$, NO$_3^-$, NHR$^2$NR$^2_2$, NH$_3^+$, NH$_2$R$^{(2+)+}$, NR$^2_2{}^+$ where R=hydrocarbon radical, glycol, glycerol, polyglycol, polyglycerol; F, Cl, I and/or Br;

wherein the at least one complex forming agent is selected from the group of water-soluble acids, anions and/or salts of at least one bifunctional to polyfunctional acid or ether carboxylic acid, in particular the complex forming agent corresponds to a bi-, tri-, polycarboxylic acid, bi-, tri-, polyphosphonic acid, bi-, tri-, polysulphonic acid, a bi-, tri-, polysulphate, di-, tri-, polyphosphate, a polyether carboxylic acid and/or mixed functional compound of their acids, anions and/or salts.

Examples of water-soluble ether carboxylic acids, particularly polyether carboxylic acids, are alkyl-(O-alkyl)$_c$-COOH or alkyl-(O-alkyl)-alkyl-COOH where c is equal to 1 to 200, particularly between 1 and 100, preferably with 1 to 15 C atoms. If water-soluble salts of the acids are used, they are normally present with standard gegenions, such as Na$^+$, Li$^+$, NH$_4^+$, K$^+$, Mg$^{2+}$, Ca$^{2+}$, NH$_2$R$^+$, NHR$_2^+$ and in the form of other usual cations.

Particularly suitable complexing agents are the following acids or anions and/or salts of the acids, such as oxalic acid, oxalates such as disodium oxalate, tartaric acid (meso, d and/or l) and salts thereof, aspartic acid, ether carboxylic acids such as for example CH$_3$—(CH$_2$)$_7$—(O—CH$_2$—CH$_2$)$_8$—COOH or CH$_3$—(CH$_2$)$_7$—(O—CH$_2$—CH$_2$)$_5$—COOH, ethylene dinitrilotetraacetic acid salt, such as ethylene dinitrilotetraacetic tetrasodium salt, or 1-hydroxyethylidene-(1,1-diphosphonic acid)-disodium salt.

All standard bases may be used as the bases, particularly for example alkali hydroxide, alkaline earth hydroxide and/or an organic base. Examples of standard bases are NaOH, NH$_4$OH, Mg(OH)$_2$. Other standard bases will be familiar to one skilled in the art.

The pH value is normally adjusted to a value in the range from greater than 7 up to 12, particularly to a value between 7.5 and 11, preferably to a value between 7.1 and 8. The complexing agent, particularly the complexing agent S, is preferably used in an equimolar ratio of 1:1 to the metal salt, a ratio of 2, 3 or 4 mol to one mol metal salt may also serve the purpose of the invention.

The object of the invention is also a method for producing a complexed metal salt, particularly having general formula I, and also a complexed metal salt obtainable by this method and a preferably aqueous compound containing a complexed metal salt, obtainable according to this method,
by reacting a metal salt having general formula III $$[[L_n^{m-}(Me^{p+})]] \quad (III)$$

where Me=zinc, copper, iron, cadmium, mercury, molybdenum, lead, cobalt, nickel, chromium vanadium, manganese or tungsten, where p=1, 2, 3, 4, 5 or 6, wherein p corresponds to the oxidation number of Me, where L is a ligand, wherein the ligands are derived from compounds having a hydrophobic carbon skeleton with hydrophilic groups, wherein they are usually present in the metal salt as an anion, particularly wherein the ligands are derived from at least one functionalised acid, particularly wherein L is the same or different with $1 \le n \le 20$, particularly with $1 \le n \le 10$, wherein the ligand L is derived from a molecule having general formula II $$B(R^1D)_1 \quad (II)$$

with a functional group D, wherein according to the invention D forms the metal salt with the metal, with D=—COOH, —O—SO$_3$H, —SO$_3$H, —O—PO(OH)$_2$, (—O—)$_2$—PO(OH) or —PO(OH)$_2$ and/or an anion or salt derived therefrom, wherein m in formula III corresponds to the charge number of functional group D as an anion or in the salt, with m=1, 2, 3 or 4, and particularly preferably m=1 or 2 and 1=1 or 2, wherein R$_1$ corresponds to an organic radical functionalised with B and R$^1$=substituted linear, branched and/or cyclic alkyl, alkenyl, alkylaryl, arylalkyl, alkenylaryl group having 1 to 40 C atoms, preferably 8 to 30 C atoms, particularly 8 to 24 C atoms, and the aryl group has 6 or 12 C atoms, wherein R$^1$ has at least one group B, particularly on a primary, secondary and/or tertiary C atom, particularly preferably on a secondary C atom of an alkyl group, and R$^1$ particularly preferably has a plurality of groups B, particularly 1 to 20, preferably 1 to 10, wherein B=OH, SO$_3^-$; SO$_3$H, SO$_4^-$, —O—SO$_3$H, —COOH, PO$_3^-$, PO$_3$H, PO$_4^-$, PO$_4$H, such as for example —O—PO(OH)$_2$, (—O—)$_2$—PO(OH) or —PO(OH)$_2$ and/or corresponding anions; —O-(alkyl-O—)$_a$-alkyl-OH where $1 \le a \le 200$, preferably $1 \le a \le 100$, and where alkyl=methyl, ethyl, or propyl groups, such as —O—(CH$_2$CH$_2$—O—)$_a$—CH$_2$—CH$_2$—OH or —O—(CH$_2$—O—)$_a$—CH$_2$—OH; —SH, —SR, NO$_2$, NO$_3$, —NH$_2$, —NHR$^2$,
—NR$^2{}_2$, —NH$_3{}^+$, —NH$_2$R$^{2(+)}$, —NHR$^2{}_2{}^{(+)}$, —F, —Cl, —I, —Br, glycol, glycerol, polyglycol and/or polyglycerol and/or anions or salts derived therefrom, wherein R$^2$ is the same or different and corresponds to a linear, branched and/or cyclic alkyl, alkenyl, alkylaryl group having 1 to 40 C atoms, preferably 1 to 30 C atoms, particularly 1 to 24 C atoms, and the aryl group has 6 or 12 C atoms, wherein according to the invention the metal salt consisting of metal and ligand is water-insoluble, with at least one complexing agent S, such as of a water-soluble acid, such as H$_k$S, particularly with H=A, or of a water-soluble salt, such as A$_k$S, of a water-soluble, at least bifunctional acid to polyfunctional acid or ether carboxylic acid, wherein S is selected from the group of water-soluble acids or anions thereof and/or salts of the bi-, tri-, polucarboxylic acids, bi-, tri-, polyphosphonic acids, bi-, tri-, polysulphonic acids, bi-, tri-, polysuiphates, di-, tri-, polyphosphates and/or polyether carboxylic acids and/or mixed functional compounds of the acids, anions and/or salts in accordance with the preceding definition, in the presence of water, particularly in water, and in the presence of a base. When an ether carboxylic acid is added, the resulting complex is neutral.

All standard bases may be used as the bases, particularly for example an alkali hydroxide, alkaline earth hydroxide and/or an organic base; examples of standard bases are NaOH, NH$_4$OH, Mg(OH)$_2$. Other standard bases will be familiar to one skilled in the art. The pH value is normally adjusted to a value from 7 up to 12, particularly to a value between 7.5 and 11, preferably to a value between 7.1 and 8. The complexing agent, particularly the complexing agent S, is preferably used in an equimolar ratio of 1:1 to the metal salt, a ratio of 2, 3 or 4 mol to one mol metal salt may also serve the purpose of the invention.

Cation A in the complexed metal salt formed may be the same or different, and may correspond to a hydrogen proton, an organic cation and/or a metal cation, in accordance with the preceding description, such as for example an alkaline earth or alkali metal cation, particularly a cation from the added base.

The metal salt, particularly having formula III, is reacted in the presence of water at a temperature between 0° C. and 100° C.; the reaction preferably takes place at a temperature from 20° C. to 80° C., particularly preferably at a temperature between 40° C. and 80° C., particularly with stirring, shaking, or other measures designed to ensure that the metal salt, the complexing agent, and the water are mixed thoroughly.

A further object of the invention is also a method for producing the complexed metal salt, particularly having general formula I, as well as a complexed metal salt obtainable by this method, and a preferably aqueous solution containing a complexed metal salt particularly having general formula I, that is obtainable according to this method,
by reacting a metal salt II at least one ligand, and at least one complexing agent, in the presence of water and in the presence of a base if applicable;
wherein a metal salt II, possibly in the form of a hydrate or solvate, preferably an inorganic metal salt II, having a metal cation that is selected particularly from zinc, copper, iron, cadmium, mercury, molybdenum, lead, cobalt, nickel, chromium, vanadium, manganese, or tungsten; and having at least one gegenion, particularly at least one inorganic gegenion, particularly a sulphate, carbonate, halide, hydroxide and/or having at least two of the name gegenions in metal salt II, is reacted with at least one ligand, particularly L, according to the preceding definition, preferably a ligand having the general formula II, wherein the ligand itself is used, and with at least one complexing agent, particularly S or H$_k$S, in accordance with the previous definition of complexing agents, in the presence of water and possibly in the presence of a base.

The complexed metal salt may be recovered by removing the water, wherein the metal salt preferably has a residual moisture.

Metal salt II is reacted in the presence of water at a temperature between 0° C. and 100° C.; the reaction preferably takes place at a temperature from 20° C. to 80° C., particularly preferably at a temperature between 40° C. and 80° C., particularly with stirring, shaking, or other measures designed to ensure that the metal salt II, the ligand, the complexing agent, and the water are mixed thoroughly. The list of substances suitable for use as the base is the same as in the preceding.

According to the invention, the complexed metal salt, in particular the complexed metal salt having general formula I, is obtained; in particular it is isolated as a solid by crystallisation, evaporation, precipitation, spray drying, or some other method. This is usually carried out at an elevated temperature and possibly also reduced pressure, for example at 60° C. to 80° C. and possibly under reduced pressure.

A preferred aqueous compound consists of the complexed metal salt and water, particularly a complexed metal salt according to formula I, and possibly also of non-bonded ligands, complexing agents and/or bases, wherein the bases are selected from alkaline earth and/or alkali hydroxides. The aqueous composition according to the invention, containing a complexed metal salt, particularly a complexed metal salt according to formula I, may also contain other auxiliary materials and/or active agents, such as emulsifiers, thickeners, and so on, besides other normal additives, that will enable the aqueous compound to be transferred to a cosmetic formulation for example a formulation as a cleaning agent, if such is required.

A preferred compound containing a complexed metal salt, particularly a complexed metal salt according to formula I, may also contain other auxiliary materials, solvents, and/or active agents such as emulsifiers, thickeners, and so on, besides other normal additives, that will enable a non-aqueous compound to be transferred to a formulation if such is required.

The content of complexed metal salts in the composition may be between 0.1% by weight and 99% by weight, particularly between 0.1 and 75% by weight, preferably between 0.1 and 50% by weight, especially preferably between 0.1 and 15% by weight.

A further object of the invention is on the one hand the use of the complexed metal salt, particularly having general formula I, or the use of a compound containing the complexed metal salt for chemically binding, particularly adsorbing, pollutants and/or odorous substances, particularly pollutants and/or odorous substances with electron donor properties. Typical fields of application are formulations having a deodorising or neutralising effect for hygienic and/or cosmetic purposes, domestic cleaning agents, industrial cleaning agents, adsorbers in filters, formulations for use in domestic or commercial animal care, formulations for the treatment and/or modification of textile fibres, fabrics, or in detergent compounds and pharmaceutical formulations, and other conceivable fields of applications for such formulations or compounds.

Alternatively, the complexed metal salt or a compound containing the complexed metal salt, particularly having general formula I, may also be used to treat and/or modify substrates or substrate surfaces. The treatment and/or modification of substrates or surfaces may be carried out by vaporising a compound that contains the complexed salt, by separating the complex metal salt on the surface or the substrate. Typical substrates are textile materials, silicates, silicon dioxide, titanium dioxide, cardboard, activated charcoal, plastics, and many other conceivable carrier materials, to which the complexed metal salts may be applied.

In the context of the present invention, it was thus surprisingly found that metal soaps may be converted to complexes that are water-soluble and retain their deodorising properties. In contrast to the related art, for this, the following is required: Zn soap, complexing agent, water, and a base (for example NaOH) if required for stabilising the pH value and the associated conversion to the complexed metal salts according to the invention.

As was described previously, the complexing agents are preferably anions of bi-, tri- and polycarboxylic acids, anions of bi-, tri- and polyphosphonic acids, anions of bi-, tri- and polysulphonic acids, anions of all mixed forms of the acids listed above, anions of water-soluble ether carboxylic acids R—O(—C—C—O)n-C—COO$^-$, di-, tri-, polysulphates, di-, tri-polyphosphates, and mixed forms thereof.

Surprisingly, it was found that an acid function, preferably exactly one acid function, of the complexing agent (for example carboxylate, phosphonate, sulphonate, sulphate, phosphate, and so on) forms a coordinate and/or ionic bond directly with the metal atom. It was also discovered, surprisingly, that the complex thus created generally only becomes water-soluble if the pH value is adjusted with an alkaline solution such that the remaining acid functions, which do not complex with the metal, are completely deprotonised. The complex then becomes negatively charged, and thus water-soluble.

The complexes according to the invention are produced generally, as described in the preceding, by reacting the complexing agents with the metal soap in the heat in the solvent water. Adding OH$^-$ ions in the heat with stirring or shaking quickly causes the complex formed to dissolve in the water. This complex remains in solution after cooling. A clear liquid remains, which is also stable in the cold.

The applicant succeeded in showing that the new complexes created in this way are surface-active. The complexes lower surface tension and for example foam vigorously in aqueous solution. Because of their surface activity, these new complexes are now able to adsorb at the water/air or water/oil interface. Surprisingly, these complexes are then, and only then, able to chemically bind gas-phase compounds containing sulphur and nitrogen as well as carboxylic acids from the gas phase/atmosphere effectively.

Moreover, the new complex compounds may be applied to any solid carrier materials. If the solvent water is evaporated, the salts of the new complex compounds remain on the solid body materials. The acid functions of the complexing agent are unsaturated in the dry state by a cation (for example Na$^+$). In the dry state, these solid body materials (=solid body+complex) are then suitable for adsorbing the pollutants described above from the gas phase/atmosphere and from organic solvents, in which case a content of residual moisture should be present. The residual moisture or water content is necessary to enable the pollutants to be adsorbed. As a rule, the absolutely anhydrous complexes are not able to absorb pollutants. The residual moisture or water content relative to the complete system consisting of complex and residual moisture should be between 0.5 and 5% by weight, particularly between 0.5 and 2.5% by weight, particularly preferably from 0.5 to 1% by weight. Absolutely dry, that is to say anhydrous complexes may be reactivated by wetting, in the presence of atmospheric moisture or by dissolving in water.

The new complex compounds may also be obtained in the form of solid salts by evaporating the solvent water. The salts absorb the pollutants described above from the gas phase and from organic solvent, particularly if the salts have the residual moisture content described.

A formal representation of the structure of these surface-active complexes and their mechanism of action is shown in figure one, based on the example of the metal salt $L_1$-Me-$L_2$.

In this context, the ligand L and the pollutant-absorbing metal salt should preferably have the following properties:

The non-complexed metal salt should be water-insoluble. The ligands L in the metal salt are accordingly hydrophobic, and as pure substances they too are insoluble in water. However, the ligands must have a hydrophilic group as substituents. Hydrophilic groups are for example —OH, —SO$_3^-$, SO$_3$H, —SO$_4^-$, SO$_4$H, —COO$^-$, —COOH, —PO$_3^-$PO$_3$H, PO$_4^-$, PO$_4$H, —O—(C—C—O—)$_n$—C—C—OH (n=1, 2, ... N), —SH, —S$^-$, —SR, NO$_2$, NO$_3^-$, —NH$_2$, —NHR, —NR$_2$, —NH$_3^+$, —NH$_2$R$^+$, —NHR$_2^+$, glycols, glycerol, polyglycols, polyglycerols, F, Cl, I, Br, and so forth.

It was found that this conformation of substituents is necessary because the metal salt becomes water-soluble and surface-active when the new complex is produced. The ligands are aligned parallel to the interface at the water/air or water/oil interface. This means that the metal atom is sterically accessible for coordinate and/or ionic bonding with the pollutant molecules.

The new, surface-active complexes are capable of chemically binding odoriferous substances and pollutants of the kind described earlier.

Possible applications include the manufacture of deodorising or pollutant neutralising and adsorbing formulations for hygiene and/or cosmetic purposes, domestic cleaning agents, industrial cleaning agents, adsorbers in filters, formulations for use in domestic and commercial animal care, formulations for the treatment of textile fibres and fabrics, detergent compounds and the like.

According to a particularly preferred embodiment of the invention, the complexes according to the invention may be represented by the following formula

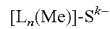

$[L_n(Me)]-S^{k-}$ wherein:
Me are metals such as zinc, copper, iron, cadmium, mercury, molybdenum, lead, cobalt, nickel, chromium, vanadium, manganese and tungsten;

$L_n$ are ligands, wherein: $L_1=L_2=\ldots=L_{n-1}=L_n$ (identical ligands) or wherein the ligands may also be different, such as for example $L_1 \neq L_2 = \ldots = L_{n-1}=L_n$;

Ligands may be:
Functionalised fatty acids: fatty acids whose hydrophobic alkyl chains carry in the side chain through one or more groups of the following kind: —OH, —SO$_3^-$, SO$_3$H, —SO$_4^-$, SO$_4$H, —COO$^-$, —COOH, —PO$_3^-$, PO$_3$H, PO$_4^-$, PO$_4$H, —O—(C—C—O—)$_n$—C—C—OH (n=1, 2, ... N), —SH, —S$^-$, —SR, NO$_2$, NO$_3^-$, —NH$_2$, —NHR, —NR$_2$, —NH$_3^+$, —NH$_2$R$^+$, —NHR$_2^+$, F, Cl, I, Br;

Functionalised alkyl sulphates, alkyl sulphonates, whose hydrophobic alkyl chains carry in the side chain through one or more groups of the following kind: —OH, —SO$_3^-$, SO$_3$H, —SO$_4^-$, SO$_4$H, —COO$^-$—COOH, —PO$_3^-$PO$_3$H, PO$_4^-$, PO$_4$H, —O—(C—C—O—)$_n$—C—C—OH (n=1, 2, ... N), —SH, —S$^-$, —SR, NO$_2$, NO$_3^-$, —NH$_2$, —NHR, —NR$_2$, —NH$_3^+$, —NH$_2$R$^+$, —NHR$_2^+$, F, Cl, I, Br;

Functionalised alkyl phosphates, alkyl phosphonates, whose hydrophobic alkyl chains carry in the side chain through one or more groups of the following kind: —OH, —SO$_3^-$, SO$_3$H, —SO$_4^-$, SO$_4$H, —COO$^-$—COOH, —PO$_3^-$PO$_3$H, PO$_4^-$, PO$_4$H, —O—(C—C—O—)$_n$—C—C—OH (n=1, 2, ... N), —SH, —S$^-$, —SR, NO$_2$, NO$_3^-$, —NH$_2$, —NHR, —NR$_2$, —NH$_3^+$, —NH$_2$R$^+$, —NHR$_2^+$, F, Cl, I, Br Functionalised aromatic carboxylic acids, sulphates, sulphonates, phosphates, phosphonates, which carry in the side chain one or more groups of the following kind: —OH, —SO$_3^-$, SO$_3$H, —SO$_4^-$, SO$_4$H, —COO$^-$—COOH, —PO$_3^-$PO$_3$H, PO$_4^-$, PO$_4$H, —O—(C—C—O—)$_n$—C—C—OH (n=1, 2, ... N), —SH, —S$^-$, —SR, NO$_2$, NO$_3^-$, —NH$_2$, —NHR, —NR$_2$, —NH$_3^+$, —NH$_2$R$^+$, —NHR$_2^+$, F, Cl, I, Br S is the solubiliser or complexing agent:
The water-soluble acids or salts of
bi-, tri- and polycarboxylic acids
bi-, tri- and polyphosphonic acids
bi-, tri- and polysulphonic acids
hybrid forms of the salts listed above
water-soluble ether carboxylic acids R—(—O—C—C)$_n$—COOH and
R—(O—C—C)$_n$—
C—COO$^-$ and derivatives thereof
di-, tri- and polysulphates,
di-, tri- and polyphosphates and hybrid forms thereof are used as complexing agent S.

The resulting surface-active complex is negatively charged to the factor of k; in the case of ether carboxylic acids, it has charge 0.

Upon reading the description, a person skilled in the art will easily recognise and understand further configurations, modifications and variations of the present invention without exceeding the scope of the present invention.

In the following, the present invention will be illustrated with reference to exemplary embodiments, which do not limit the present invention in any way.

Embodiments

General Example I

The water-insoluble metal salts, particularly of the general formula III $[[L_n^{m-}(Me^{p+})]]$ described previously, are dissolved in heat at 40° C. to 80° C. with the addition of the corresponding complexing agent, such as complexing agent S, particularly of acid H$_k$S or of the salt of the complexing agent A$_k$S and while adding a base such as caustic soda (NaOHaq).

General Example II

The water-insoluble metal compound L$_n$Me is dissolved in heat at 40 to 80° C. with the addition of the corresponding complexing agent H$_k$S or of the salt of the complexing agent and with the addition of a base (for example, NaOH).

General Example III

According to one alternative, the complexed metal salts may also be obtained from their raw materials. For this, usually at least one ligand, particularly a functionalised fatty acid, a metal salt II, preferably an inorganic metal salt such as Me$^{p+}$ with at least one gegenion, for example a metal sulphate, metal carbonate, metal halide, metal hydroxide or another usual salt is reacted directly with a complexing agent and water, possibly with the addition of a base, for example sodium hydroxide, to obtain the complexed metal salt.

For this, the complexing agent is added in water to the ligand, particularly a functionalised fatty acid, preferably in a molar ratio of 1:1 or stoichiometrically with reference to the coordinate groups and/or groups to be ionised. The ligand, in this case the fatty acid, and the complexing agent, are dissolved by adding a base. Then an aqueous solution of the metal salt is added to the fatty acid in the corresponding molar ratio. A base is added to set the pH to a value in the range between 7 and 12, particularly to a pH value between 7.5 and 11, preferably to a value between 7.1 and 8.

Example 1

The zinc soap zinc ricinoleate [Zn(C$_{18}$H$_{33}$Os)$_2$] as the metal salt is reacted with the complexing agent oxalic acid. For this, one gram zinc ricinoleate is weighed and placed in a 100 ml beaker together with 1.13 g oxalic acid, and 25 ml distilled water is added. The suspension is heated to 75° C. with stirring. After the zinc ricinoleate has melted, 5 M caustic soda is added dropwise until the melted zinc ricinoleate goes into solution at a pH value of 7 to 8. Foaming is observed. Then the clear solution is cooled to room temperature. The following reaction equation represents the transformation reaction that takes place:

$$Zn(C_{18}H_{33}O_3)_2 + HOOC-COOH + 2OH^- \rightarrow$$
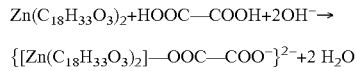
$$\{[Zn(C_{18}H_{33}O_3)_2]-OOC-COO^-\}^{2-} + 2 H_2O$$

Example 2

The zinc soap zinc ricinoleate [Zn(C$_{18}$H$_{33}$O$_3$)$_2$] as the metal salt is reacted with the complexing agent 1-hydroxyethylidene-(1,1-diphosphonic acid) (HEDP). For this one gram zinc ricinoleate is weighed and place in a 100 ml beaker together with 0.560 g 60% 1-Hydroxyethylidene-(1,1-diphosphonic acid), and 25 ml distilled water is added. The suspension is heated to 75° C. with stirring. After the zinc ricinoleate has melted, 5 M caustic soda is added dropwise until the melted zinc ricinoleate goes into solution. Foaming is observed.

In accordance with example 1 or 2, zinc ricinoleate [Zn (C$_{18}$H$_{33}$O$_3$)$_2$] was reacted with aspartic acid as the complexing agent.

Alternatively, the corresponding water-soluble salts of the complexing agents may also be reacted directly with zinc ricinoleate [Zn(C$_{18}$H$_{33}$O$_3$)$_2$]. Complexed metal salts were also prepared in water with the complexing agents ethylene dinitriloacetic acid tetrasodium salt, 1-Hydroxyethane-(1,1-diphosphonic acid)-disodium salt, oxalic acid disodium salt, tartaric acid disodium salt (meso, d and/or l).

Example 3

Preparation of a 33% ZnRi/LF2 Solution 5 g zinc ricinoleate (ZnRi) and 10 g ether carboxylic acid (LF2=CH$_3$—(CH$_2$)$_7$—(OCH$_2$CH$_2$)$_8$—COOH) are mixed in a 100 ml beaker and heated to about 75-80° C. while stirring. After cooling to room temperature in a water bath, a highly viscous, slightly cloudy solution is obtained. This solution may be diluted with distilled water while cooling. With the dilution, the slightly cloudy solution usually becomes clear again. The complex obtained $$\{[Zn(C_{18}H_{33}O_3)_2][CH_3-(CH_2)_7-(OCH_2CH_2)_8- COO]\}$$

is surface-active in water and the aqueous solution is capable of absorbing NH$_3$ and H$_2$S. The complex may be applied to solid carriers by evaporating the solvent water. The modified, solid carrier materials are able to absorb NH$_3$ and H$_2$S.

Example 4

Preparation of a 2.5% Solution of the Complex [CH$_3$—(CH$_2$)$_7$—(OCH$_2$CH$_2$)$_8$—COO]$_3$Zn}— from ZnCO$_3$ and Ether Carboxylic Acid 2.5 g basic zinc carbonate and 97.5 g ether carboxylic (LF2=CH$_3$—(CH$_2$)$_7$—(OCH$_2$CH$_2$)$_8$—COOH) are mixed in a 100 ml beaker and heated to about 100-105° C. while stirring. After cooling to room temperature in a water bath, a viscous, cloudy solution is obtained. This solution may be diluted with distilled water while stirring. With the dilution, the solution usually becomes clear again. The complex can be applied to solid carriers by evaporating the solvent water. The modified solid carrier materials are able to absorb NH$_3$ and H$_2$S.

Example 5

1.5 g zinc ricinoleate (0.005 mol) is added to 20 ml distilled water and 0.52 g HEDP (0.025 mol; HEDP=1-Hydroxyethane-(1,1-diphosphonic acid)-disodium salt) in a 250 ml Erlenmeyer flask. Then, 6M caustic soda is added dropwise until a clear solution is obtained, the pH value is at about 8.1. Then 0.725 g (0.0025 mol) zinc sulphate heptahydrate, dissolved in 10 ml water, is transferred dropwise by pipette. A further 6M caustic soda is added dropwise to yield a clear solution at pH 8. This solution contains the new surface-acting complex.

The measurement of pollutant adsorption is illustrated in greater detail with reference to the embodiments of FIGS. 1 to 6:

FIG. 1: Shows a possible idealised structure of the surface-acting complexes.

Figure 2:
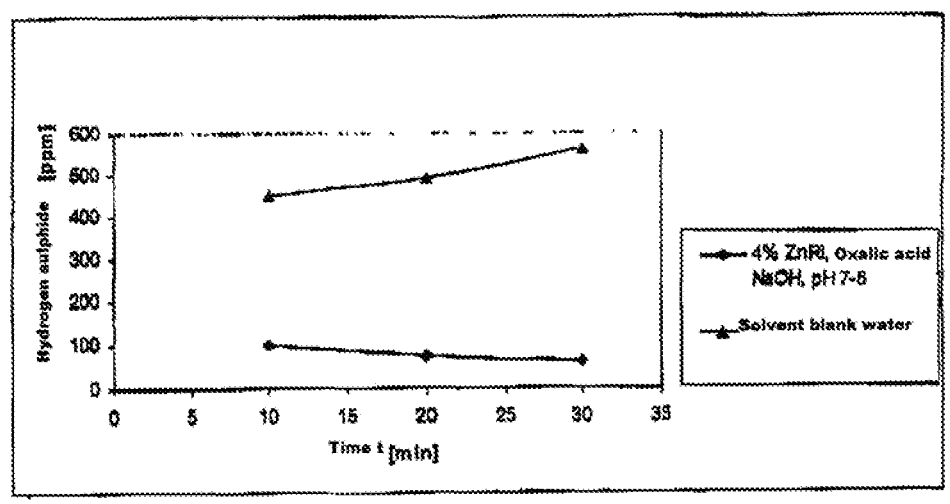
FIG. 2 provides a plot of the adsorption of $H_2S$ (1 ml, 1:100 diluted, saturated sodium sulphite solution, 100 μl 99% HAC, acetic acid) on the active substance complex $[Zn(C_{18}H_{33}O_3)_2]$—OOC—COO$^-$ in a liquid system at pH 7-8, adjusted with NaOH, with Ri=$(C_{18}H_{33}O_3)_2$, compared with a blank sample of water over time.

FIG. 2: Shows the adsorption of H$_2$S (1 ml, 1:100 diluted, saturated sodium sulphite solution, 100 μl 99% HAC, acetic acid) on the active substance complex [Zn(C$_{18}$H$_{33}$O$_3$)$_2$]—OOC—COO$^-$ in a liquid system at pH 7-8, adjusted with NaOH, with Ri=(C$_{18}$H$_{33}$O$_3$)$_2$; compared with a blank sample of water.

Figure 3:
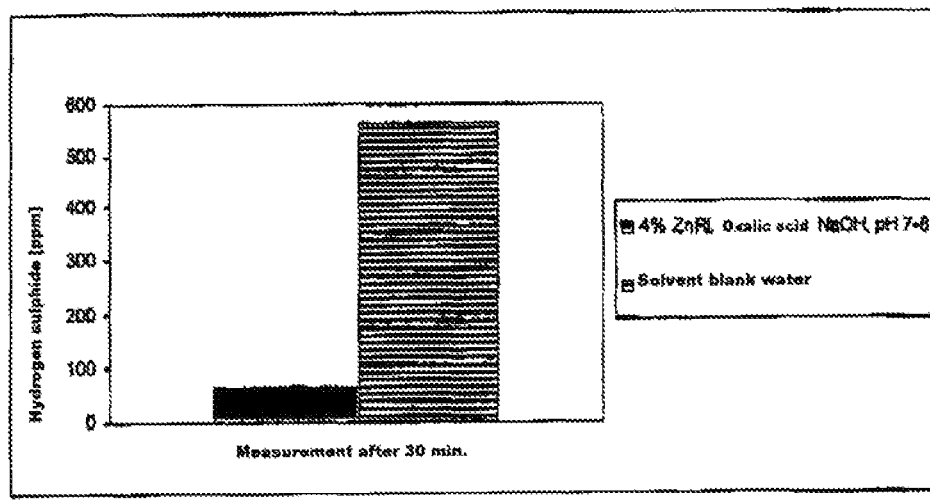
FIG. 3 provides a plot of the hydrogen sulphide content after 30 minutes of adsorption on the active substance complex $[Zn(C_{18}H_{33}O_3)_2]$—OOC—COO$^-$ in a liquid system at pH 7-8, adjusted with NaOH, with Ri=$(C_{18}H_{33}O_3)_2$ compared with a blank sample of water.

FIG. 3: Shows the hydrogen sulphide content after 30 minutes of adsorption on the active substance complex [Zn (C$_{18}$H$_{33}$O$_3$)$_2$]—OOC—COO$^-$ in a liquid system at pH 7-8, adjusted with NaOH, with Ri=(C$_{18}$H$_{33}$O$_3$)$_2$ compared with a blank sample of water.

Figure 4:
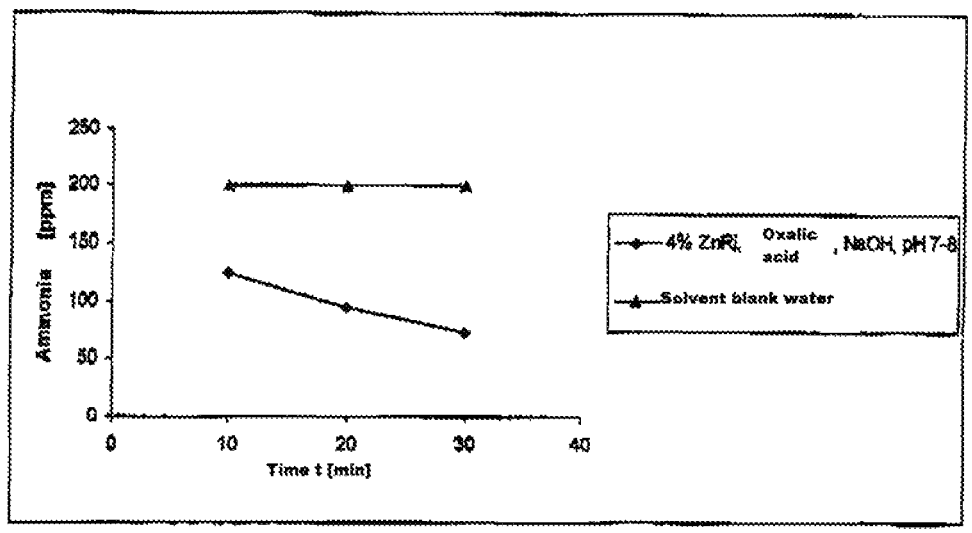
FIG. 4 provides a plot of the adsorption of ammonia ($NH_3$) (30 μl, 1:5 diluted 30% ammonia solution, 1 ml adsorbens) on the active substance complex $[Zn(C_{18}H_{33}O_3)_2]$—OOC—COO$^-$ in a liquid system at pH 7-8, adjusted with NaOH, with Ri=$(C_{18}H_{33}O_3)_2$ compared with a blank sample of water.

FIG. 4: Shows the adsorption of ammonia (NH$_3$) (30 μl, 1:5 diluted 30% ammonia solution, 1 ml adsorbens) on the active substance complex [Zn(C]$_{18}$H$_{33}$O$_3$)$_2$]—OOC—COO$^-$ in a liquid system at pH 7-8, adjusted with NaOH, with Ri= (C$_{18}$H$_{33}$O$_3$)$_2$ compared with a blank sample of water.

Figure 5:
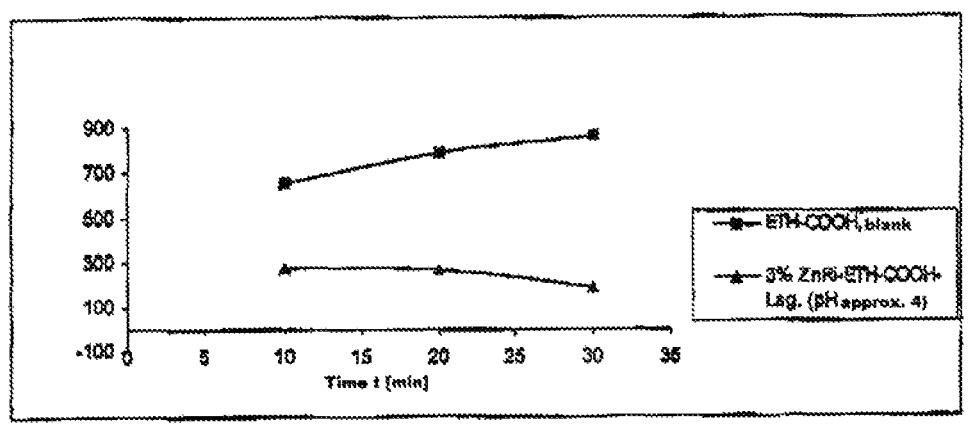
FIG. 5 provides a plot of the adsorption of hydrogen sulphide ($H_2S$) (1 ml adsorbens, 1 ml, 1:100 diluted, saturated sodium sulphite solution, 100 µl 99% acetic acid) on the active substance complex $CH_3$—$(CH_2)_7$—$(-OCH_2CH_2)_8$—COO—$[Zn(C_8H_{33}O_3)_2]$ in a liquid system at pH 4 with Ri=$(C_{18}H_{33}O_3)_2$ compared with a blank sample with ether carboxylic acid $CH_3$—$(CH_2)_7$—$(OCH_2CH_2)_8$—COOH.

FIG. 5: Shows the adsorption of hydrogen sulphide (H$_2$S) (1 ml adsorbens, 1 ml, 1:100 diluted, saturated sodium sulphite solution, 100 μl 99% acetic acid) on the active substance complex CH$_3$—(CH$_2$)$_7$—(—OCH$_2$CH$_2$)$_8$—COO— [Zn(C$_{,8}$H$_{33}$O$_3$)$_2$] in a liquid system at pH 4 with Ri= (C$_{18}$H$_{33}$O$_3$)$_2$ compared with a blank sample with ether carboxylic acid CH$_3$—(CH$_2$)$_7$—(OCH$_2$CH$_2$)$_8$—COOH.

Figure 6:
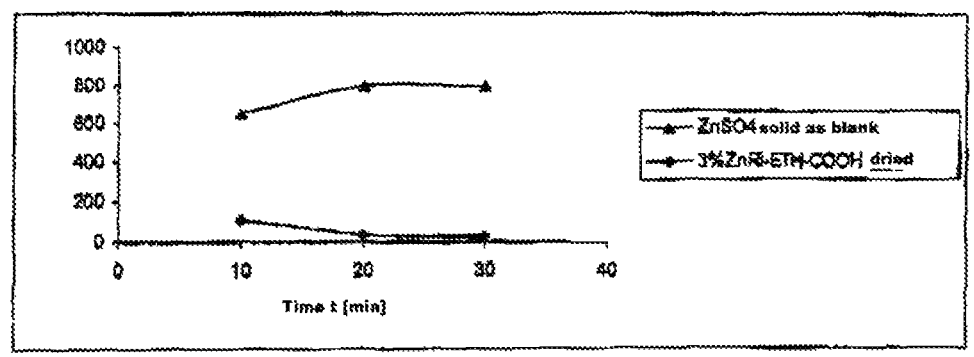
FIG. 6 provides a plot of the adsorption of hydrogen sulphide ($H_2S$) (5 ml adsorbens dried at 80° C., 1 ml, 1:100 diluted, saturated sodium sulphide solution, 100 µl (99%)) on the active substance complex $CH_3$—$(CH_2)_7$—$(OCH_2CH_2)_8$—COO—$[Zn(C_{18}H_{33}O_3)_2]$ as solid with Ri=$(Ci_8H_{33}O_3)_2$ compared with a blank sample of zinc sulphate.

FIG. 6: Shows the adsorption of hydrogen sulphide (H$_2$S) (5 ml adsorbens dried at 80° C., 1 ml, 1:100 diluted, saturated sodium sulphide solution, 100 μl (99%)) on the active substance complex CH$_3$—(CH$_2$)$_7$—(OCH$_2$CH$_2$)$_8$—COO—[Zn (C$_{18}$H$_{33}$O$_3$)$_2$] as solid with Ri=(C$_{18}$H$_{33}$O$_3$)$_2$ compared with a blank sample of zinc sulphate.

Ether carboxylic acid is abbreviated to ETH— COOH=CH$_3$—(CH$_2$)$_7$—(OCH$_2$CH$_2$)$_S$—COOH in FIG. 6.

The invention claimed is:

1. A method for producing a complexed metal salt of the general formula I $$[[L_n^m-(Me^{p+})]-S_x^{k+}] \cdot zA^{y+} \qquad (I)$$

with Me as the metal, wherein Me=zinc;
wherein p=1, 2, 3, 4, 5 or 6, and p corresponds to the oxidation number of Me;

with L as ligand, wherein L is the same or different, with $1 \leq n \leq 20$, wherein the ligand L is derived from a molecule having general formula II:

$$B(R^1\text{-}D)_l \quad (II)$$

with a functional group D=-COOH, —O—SO$_3$H, —SO$_3$H, —O—PO(OH)$_2$, (—O—)$_2$—PO(OH) or —PO(OH)$_2$ or an anion or salt derived therefrom, wherein m in formula I corresponds to the charge number of functional group D as an anion or in the salt with m=1, 2, 3 or 4, and l=1 or 2, and wherein $R^1$ corresponds to an organic radical functionalised with B and $R^1$=substituted linear, branched or cyclic alkyl, alkenyl, alkylaryl, arylalkyl, alkenylaryl group having 1 to 40 C atoms, wherein $R^1$ has at least one group B, and wherein B=OH, SO$_3^-$; SO$_3$H, SO$_4^-$, —O—SO$_3$H, —COOH, PO$_3^-$, PO$_3$H$_4$, PO$_4^-$, PO$_4$H, —O-(alkyl-O-)$_a$-alkyl-OH where $1 \leq a \leq 200$, and alkyl=methyl, ethyl, or propyl group, —SH, —SR, NO$_2$, NO$_3$, —NH$_2$, —NHR$^2$, —NR$^2_2$, —NH$_3^+$, —NH$_2$R$^{2(+)}$, —NHR$^{2(+)}_2$, —F, —Cl, —I, —Br, glycol, glycerol, polyglycol or polyglycerol or anions or salts derived therefrom, wherein $R^2$ is the same or different and corresponds to a linear, branched or cyclic alkyl, alkenyl, alkylaryl group having 1 to 40 C atoms;

wherein S is selected from the group of water-soluble acids, anions or salts of the bi-, tri-, polycarboxylic acids, bi-, tri-, polyphosphonic acids, bi-, tri-, polysulphonic acids, bi-, tri-, polysulphates, di-, tri-, polyphosphates or polyether carboxylic acids or mixed functional compounds of the acids, anions or salts, where x=1, 2, 3 or 4 and wherein k corresponds to the charge number of the anion of S, where $1 \leq k \leq 20$, wherein ether carboxylic acids are understood to include carboxylic acids having the composition alkyl-(O-alkyl)$_c$-COOH or alkyl-(O-alkyl)$_c$-alkyl-COOH where c is equal to 1 to 200 C atoms; and wherein A is the same or different and corresponds to a hydrogen proton, an organic cation or a metal cation, and where z is equivalent to a whole number between $0 \leq z \leq 20$, and wherein y corresponds to the charge number of A, with y=1 or 2, wherein the amount is from $x \cdot k = z \cdot y$, the method comprising reacting a metal salt with ligands and at least one complexing agent in the presence of water and optionally in the presence of a base, wherein the metal is present as a cation and zinc, and wherein the ligands are derived from at least one functionalised fatty acid, alkenyl carboxylic acid or aryl carboxylic acid, alkyl sulphonate, aryl sulphonate, alkyl sulphate, aryl sulphate, alkyl phosphate, aryl phosphate, alkyl phosphonate or aryl phosphonate, or from correspondingly alkenyl-, arylalkenyl-, or arylalkyl functionalised acids, wherein the alkyl, alkenyl or aryl groups may be functionalised with at least one of the following groups —OH, SO$_3^-$SO$_3$H, SO$_4^-$, SO$_4$H, COO$^-$, COOH, PO$_3^-$, PO$_3$H, PO$_4^-$, PO$_4$H;

O-(alkyl-O-)$_a$-alkyl-OH where a=1 to 200, and having alkyl=methyl-, ethyl- or propyl group, SH, S$^-$, SR, NO$_2$, NO$_3^-$, NH$_2$, NHR, NR$_2$, NH$_3^+$, NH$_2$R$^+$, NHR$_2^+$, where R=hydrocarbon radical, glycol, glycerol, polyglycol, polyglycerol; F, Cl, I or Br; and wherein the at least one complexing agent is selected from the group of anions or salts of the bi-, tri-, polycarboxylic acids, bi-, tri-, polyphosphonic acids, bi-, tri-, polysulphonic acids, bi-, tri-, polysulphates, di-, tri-, polyphosphates, polyether carboxylic acids or mixed functional compounds of these acids, anions or salts.

2. The method as recited in claim 1, wherein a metal salt having general formula III

$$[[L_n^{m-}(Me^{p+})]] \quad (III)$$

where Me=zinc;

wherein L is a ligand, wherein L is the same or different, with $1 \leq n \leq 20$, wherein the ligand L is derived from a molecule having general formula II

$$B(R^1D)_l \quad (II)$$

with a functional group D=-COOH, —O—SO$_3$H, —SO$_3$H, —O—PO(OH)$_2$, (—O—)$_2$—PO(OH) or —PO(OH)$_2$ or an anion or salt derived therefrom, wherein m in formula III corresponds to the charge number of functional group D as an anion or in the salt, with m=1 or 2 and l=1 or 2, wherein $R^1$ corresponds to an organic radical functionalised with B and $R^1$=substituted linear, branched or cyclic alkyl, alkenyl, alkylaryl, arylalkyl, alkenylaryl group having 1 to 40 C atoms, wherein $R^1$ has at least one group B on a primary, secondary or tertiary C atom, with B=OH, SO$_3^-$; SO$_3$H, SO$_4^-$, —O—SO$_3$H, —COOH, PO$_3^-$, PO$_3$H, PO$_4^-$, PO$_4$H, —O—PO(OH)$_2$, (—O—)$_2$—PO(OH) or —PO(OH)$_2$ or corresponding anions; —O-(alkyl-O-)$_a$-alkyl-OH where $1 \leq a \leq 100$, and where alkyl=methyl, ethyl, or propyl groups, —O—(CH$_2$CH$_2$—O—)$_a$—CH$_2$—CH$_2$—OH or —O—(CH$_2$—O—)$_a$—CH$_2$—OH; —SH, —SR, NO$_2$, NO$_3$, —NH$_2$, —NHR$^2$, —NR$^2_2$, —NH$_3^+$, —NH$_2$R$^{2(+)}$, —NHR$^{2(+)}_2$, —F, —Cl, —I, —Br, glycol, glycerol, polyglycol or polyglycerol or anions or salts derived therefrom, wherein $R^2$ is the same or different and corresponds to a linear, branched or cyclic alkyl, alkenyl, alkylaryl group having 1 to 40 C atoms, is reacted with at least one complexing agent S, wherein S is selected from the group of bi-, tri-, polycarboxylic acids, bi-, tri-, polyphosphonic acids, bi-, tri-, polysulphonic acids, bi-, tri-, polysulphates, di-, tri-, polyphosphates or polyether carboxylic acids or mixed functional compounds of the acids, anions or salts in the presence of water and optionally in the presence of a base.

3. The method as recited in claim 1, wherein the reaction takes place in the presence of water at temperature between 0° C. and 100° C.

4. The method as recited in claim 1, wherein an alkaline hydroxide, alkaline earth hydroxide or an inorganic base is added.

5. The method as recited in claim 1, wherein the complexed metal salt dissolved in water having general having formula I is obtained.

6. The method as recited in claim 1, wherein the complexed metal salt having general having formula I is produced when an inorganic metal salt II having a metal cation that is zinc; and having at least one gegenion, and having at least one ligand L and with at least one complexing agent S or H$_k$S is reacted in the presence of water and optionally in the presence of a base.

* * * * *